US006388453B1

(12) United States Patent
Greer

(10) Patent No.: US 6,388,453 B1
(45) Date of Patent: May 14, 2002

(54) SWEPT-FREQUENCY DIELECTRIC MOISTURE AND DENSITY SENSOR

(76) Inventor: Bryan D. Greer, 14440 Guarani St., Andover, MN (US) 55304

(*) Notice: Subject to any disclaimer, the term of this patent is extended or adjusted under 35 U.S.C. 154(b) by 0 days.

(21) Appl. No.: 09/236,411

(22) Filed: Jan. 25, 1999

(51) Int. Cl.[7] ............................................. G01R 27/26
(52) U.S. Cl. ..................................... 324/667; 324/664
(58) Field of Search ........................... 324/660, 659, 324/664, 667, 686

(56) References Cited

U.S. PATENT DOCUMENTS

| | | | | |
|---|---|---|---|---|
| 3,684,953 A | * | 8/1972 | Grant | 324/667 |
| 3,826,979 A | * | 7/1974 | Steinmann | 361/178 |
| 4,058,766 A | * | 11/1977 | Vogel et al. | 324/667 |
| 4,168,466 A | | 9/1979 | Boldt | |
| 4,322,678 A | | 3/1982 | Capots | |
| 4,370,611 A | | 1/1983 | Gregory | |
| 4,426,616 A | * | 1/1984 | Maier | 324/658 |
| 4,433,286 A | | 2/1984 | Capots | |
| 4,499,111 A | | 2/1985 | Oetiker | |
| 4,837,500 A | * | 6/1989 | Abbringh | 324/660 |
| 4,853,614 A | | 8/1989 | Carver | |
| 4,881,025 A | | 11/1989 | Gregory | |
| 4,932,243 A | | 6/1990 | Suh | |
| 5,166,674 A | | 11/1992 | Vranish | |
| 5,326,163 A | | 7/1994 | Langton | |
| 5,412,327 A | * | 5/1995 | Meinen | 324/686 |
| 5,461,320 A | * | 10/1995 | Strack et al. | 324/662 |
| 5,521,515 A | | 5/1996 | Cambell | |
| 5,666,061 A | | 9/1997 | Assenheim | |

OTHER PUBLICATIONS

K.C. Lawrence, Dielectric Properties Measurements with a Flow–Through Coaxial Sample Holder, written paper for presentation at ASAE International Meeting, 1996.

K.C. Lawrence, Sensing Wheat Moisture Content Independent of Density, Written paper for presentation at ASAE International Meeting, 1997.

Stuart O. Nelson, Observation on the Density Dependence of Dielectric Properties, Journal of Microwave Power 18(2), 1983.

S.D. Powell, Use of Density–Independent Function and Microwave Measurement, Transactions of the ASAE 31(6): Nov.–Dec. 1998 p. 1875.

(List continued on next page.)

Primary Examiner—Safet Metjahic
Assistant Examiner—Vincent Q. Nguyen
(74) Attorney, Agent, or Firm—Lawrence E. Laubscher, Jr.

(57) ABSTRACT

A swept-frequency shunt-mode dielectric sensor system is used to measure complex impedance parameters such as capacitance and/or dielectric loss of an object or substance being sensed. A precision, digitally synthesized sinusoidal voltage waveform is applied to an amplifier that has a precise, consistent relationship between gain and sensed complex impedance. The amplifier output is the input to a phase-loced synchronous demodulator, which produces a signal related to capacitance and/or loss factor of the object or material sensed. This swept-frequency information is used by a microprocessor that can apply mathematical algorithms to the data to calculate bulk density simultaneously with moisture or other properties of the material.

4 Claims, 2 Drawing Sheets

OTHER PUBLICATIONS

S. O. Nelson, Dielectric Properties of Agricultural Products IEEE Transactions 26(5): Oct. 1991 p. 845.

R.J. King, Microwave Moisture Measurement of Grains IEEE Transactions 41(1): Feb. 1992 p. 111.

S.O. Nelson, Measurement and Application of Dielectric Properties of Ag. Products IEEE Transactions 41(1): Feb. 1992 p. 116.

A.W. Krasewski, Wheat Moisture Content and Bulk Density Determination, Canadian Ag. Engr. 34(4): Oct.–Dec. 1992 p. 327.

K.C. Lawrence, Radio Frequency Density–Independent Moisture Determination, Transactions of the ASAE 36(2): Mar.–Apr. 1993 p 477.

B.D. McLendon, Density Independent Microwave Measurement of Moisture Content, Transportation of the ASAE 36(3): May–Jun. 1993 p. 827.

K.C. Lawrence, Wheat Moisture Determination by Swept–Frequency Admittance Measurements, written paper for presentation at ASAE International Summer Meeting, Jun.1994.

* cited by examiner

SWEPT-FREQUENCY DIELECTRIC MOISTURE AND DENSITY SENSOR

BACKGROUND OF THE INVENTION

Devices for laboratory and on-line moisture or density measurement and identification of agricultural and other products are desirable. Two such devices which are currently available are capacitance-based sensors and microwave sensors, both of which depend on the correlation between dielectric properties and moisture content or thickness. Capacitance sensors are less expensive and easier to work with than microwave sensors, but their accuracy is less than that provided by microwave sensors. Moreover, they are largely restricted to materials with uniform dielectric properties.

The simplest type of capacitor comprises two parallel conducting plates separated by a non-conducting dielectric material. Any dielectric material which is not a vacuum will produce a larger capacitance than if a vacuum were used. Accordingly, a measurement of capacitance can provide information about the dielectric material. Capacitance sensors measure the capacitance for various dielectric materials or samples. When an AC electric field is imposed on a dielectric, it will absorb some of the field's energy. The loss factor is a measure of the amount of energy absorbed by the dielectric.

The dielectric properties of agricultural products are affected by a number of factors including moisture content, frequency, temperature, and density. Most existing capacitance based sensors measure the dielectric constant and/or loss factor of a sample at a single frequency and use this information to determine material properties such as thickness, density, or moisture content. The present invention relates to a multiple frequency capacitance sensor which measures the dielectric properties of a sample over a wide range of frequencies.

Recent advances in microprocessor technology have made possible many sensor technologies. One such technology is real-time, multiple frequency/multiple parameter dielectric or capacitive sensing which requires significant data storage and analysis. Real-time multiple frequency/multiple parameter dielectric sensing offers tremendous possibilities in material identification, improved precision of composition measurements such as moisture content, and simultaneous identification of multiple material parameters such as moisture and density.

BRIEF DESCRIPTION OF THE PRIOR ART

Multiple-frequency sensors for sensing the type of material in a sample are well known in the patented prior art as evidenced by U.S. Pat. No. 5,521,515. As disclosed therein, a voltage-controlled oscillator drives a capaciflector type shielded sensor element. The impedance magnitude is measured over a predetermined frequency range and a digital computer compares the impedance v frequency curve to stored curves of known materials in order to identify the material and as an option to measure the distance to the sample.

Shunt-mode capacitive sensing is also known for various applications but is new to the field of multiple-frequency dielectric properties measurement. Shunt-mode capacitive sensing measures the capacitance between a transmitter and a reference irrespective of any capacitance to a reference potential, rather than between a transmitter and a reference potential. This allows a simple approach to shielding, using a passive shield connected directly to a reference potential rather than an active shield which follows the transmitter's electrical potential. In addition, it allows more distinct measurements to be made for a given sensor array configuration than a sensor which measures capacitance to a reference potential, as measurements can be made from any sensor element to any other sensor element in an array rather than simply from each sensor element to a reference potential.

Multiple-parameter impedance measurement for real and imaginary portions of complex impedance is also known in the prior art. For example, single-frequency, two-parameter microwave measurements have been used in moisture sensors to allow thickness compensation with known density or density compensation with known thickness. It is known in the field of moisture sensing that two-parameter measurements generally can be used to achieve superior measurement accuracy when compared to single-parameter measurements of the same material.

Capacitive density measurements are also known in the prior art, though such systems have involved measurements at only a single frequency, limiting their effectiveness to materials which have known dielectric properties. Such devices would not be useful with hydroscopic materials such as cereal grains, which have dielectric properties which vary substantially with moisture content.

SUMMARY OF THE INVENTION

Accordingly, it is a primary object of the present invention to provide a method and apparatus for determining the bulk density and/or moisture content of a particulate sample using a capacitance sensor. At least one sinusoidal voltage signal is applied to the sensor which is arranged in a quantity of the sample to produce a change in the electrical properties of the sensor as a function of the sample. The change in the electrical properties is measured and then correlated to determine the bulk density and/or moisture content of the sample.

According to another object of the invention, the sensor is a shunt-mode dielectric sensor and the electrical properties include at least one of capacitance and dielectric loss.

The sensor may comprise at least two spaced parallel conductive plates or at least two coplanar conductive plates, while the sinusoidal voltage signal is produced by a digitally synthesized oscillator. Correlation is performed in a microcomputer using algorithms to determine the moisture content and density of the sample.

BRIEF DESCRIPTION OF THE FIGURES

Other objects and advantages of the subject invention will become apparent from a study of the following specification when viewed in the light of the accompanying drawing, in which.

DETAILED DESCRIPTION

Figure 1:
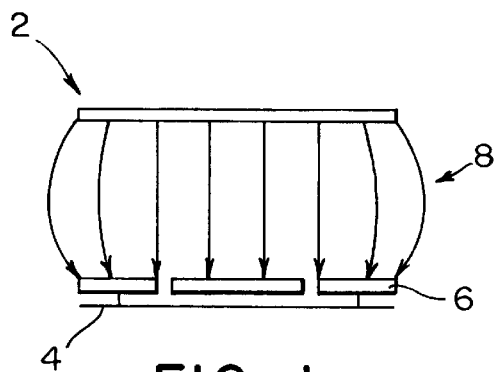
FIG. 1 is a sectional view of a first embodiment of a capacitance sensor according to the invention.
Figure 2:
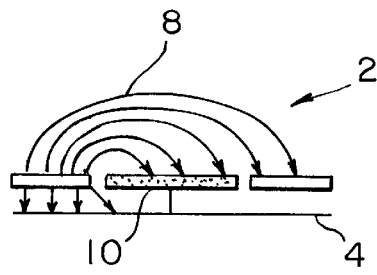
FIG. 2 is a sectional view of a second embodiment of a capacitance sensor according to the invention.

Referring first to FIGS. 1 and 2, there are shown two different versions of a capacitive sensor 2 according to the invention. In each embodiment, the sensor is in a shunt configuration, i.e. at least a two terminal device measuring complex impedance between transmitting and receiving terminals without respect to a reference potential. This configuration is different from prior capacitive sensors which are single terminal devices which measure capacitance between the terminal and a reference potential. The shunt configuration capacitive sensor is particularly beneficial in array applications (not shown) in which any terminal may be the transmitter and any other terminal may be the receiver, permitting more distinct measurements for a given number of array elements. A further advantage of shunt-mode capacitive sensors is that when they are used with virtual ground amplifier circuits (FIG. 4), a fixed reference potential can be used for shielding, rather than a signal made to follow the transmitting terminal. Moreover, parasitic capacitance to ground has no affect on the capacitance measurements, except to decrease amplifier bandwidth. This is of little consequence if amplifiers of sufficiently high bandwidth are used.

The preferred sensor is the parallel plate sensor of FIG. 1. When used with a virtual ground amplifier, the receiving terminal 4 is maintained at a reference potential by a feedback loop though it is not directly connected to the reference potential since the receiving plate actually comprises a plurality of coplanar plates 6. Thus the electric field lines 8 in the sensor behave in the same manner as in a simple two-plate parallel plate capacitor. However, only the parallel field lines toward the center of the capacitive sensing element are involved in measurement. Accordingly, the complex admittance of the sensor element will be directly proportional to the complex dielectric properties of the particulate sample arranged within the sensor.

In a measurement made with electric field lines which are not parallel to each other and perpendicular to the interface between the sensor surface and the sensed material, the field lines will distort in a manner which depends on the dielectric properties of the material and admittance will not be a simple function of dielectric properties. This is disadvantageous for precise properties measurement.

In FIG. 2, an alternate flat co-planar plate sensor 2 is shown. It projects electric fields 8 for measurement in one direction only. The shield 10 between the transmitting and receiving electrodes results in a sensor which is not particularly sensitive to very close objects, as the field lines closest to the sensor surface return to the shield, not to the receiving terminal. The sensor of FIG. 2 is useful for proximity sensing and non-contact material identification or characterization.

Figure 3:
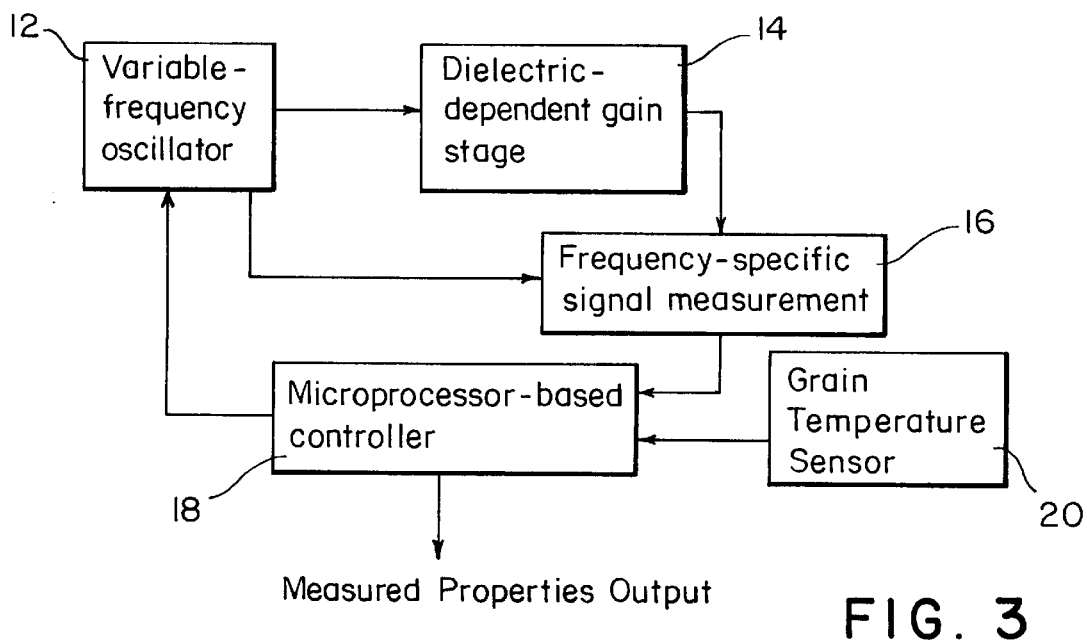
FIG. 3 is a block diagram of a multi-frequency sensor system according to a first embodiment of the invention.

Referring now to FIG. 3, a first embodiment of the sensing system according to the invention will be described in connection with the analysis of a grain sample. A variable frequency oscillator 12 produces precise waveforms at a wide range of RF frequencies, preferably between 1.0 kHz and 10 MHz. The variable frequency oscillator 12 is connected with a dielectric dependent gain stage 14 comprising an amplifier and the shunt-mode capacitive sensor. The output from the dielectric dependent gain stage is dependent on the capacitance of the sample and a loss signal. The output signal is measured by a frequency-specific signal measurement circuit 16 which also receives an input from the variable frequency oscillator 12 to eliminate the effects of noice at other frequencies. The resulting information of measurements taken at a variety of frequencies is used by a microprocessor based controller 18 to calculate via correlation the composition, thickness, and/or density of the grain. A grain temperature sensor 20 measures the grain temperature and provides an input to the controller 18 to correct for various temperatures.

In operation of the embodiment of FIG. 3, the oscillator is set to a minimum frequency and the resulting sinusoid is precisely measured. Next, the dielectric constant and/or loss factor in the capacitive sensor resulting from the sample is calculated. The steps are repeated for different frequencies and the results of each calculation are correlated in the controller to provide an indication of the properties of the sample. The correlation is preferably accomplished using a variety of multivariate analysis techniques, such as a partial least squares algorithm already used in connection with near infrared spectroscopy. For additional precision, a reference capacitor may be provided to calibrate the capacitive sensor to protect against errors introduced by thermal drift to aging of the electronic components.

Figure 4:
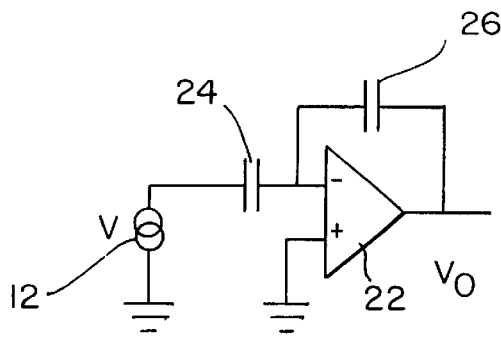
FIG. 4 is a circuit diagram of a virtual ground amplifier used for shunt-mode capacitive measurements.

In FIG. 4, there is shown in greater detail a virtual ground amplifier which serves as a sensing circuit. A variable frequency oscillator 12 is connected with an operational amplifier 22. Reference capacitor 24 is provided to stabilize the amplifier and capacitor 26 comprises the sensing plates.

Figure 5:
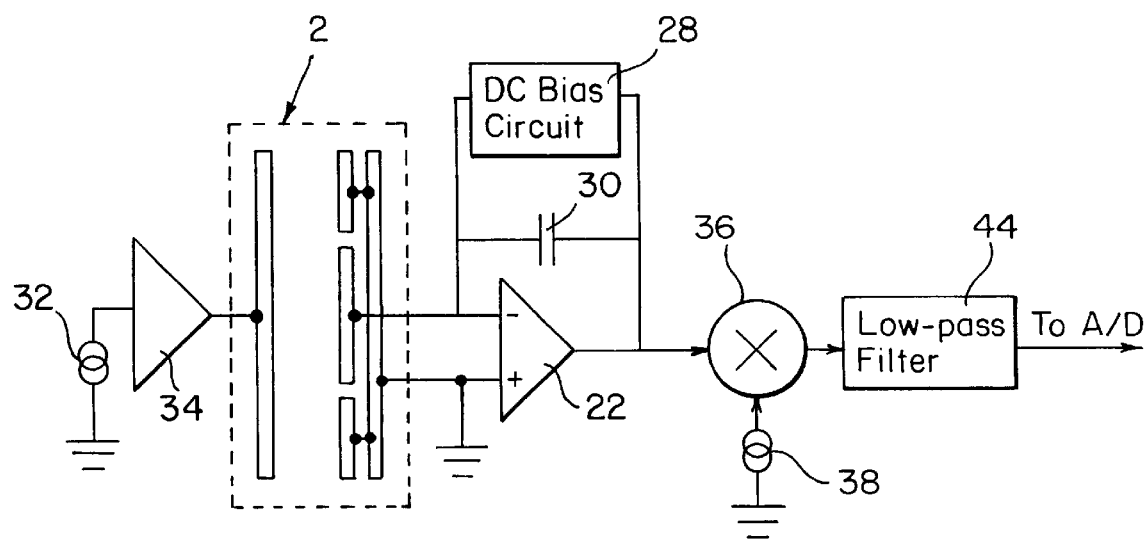
FIG. 5 is a circuit diagram of a dielectric properties measurement device including a parallel plate shunt-mode capacitive sensor element.

As shown in FIG. 5, the virtual ground amplifier 22 is connected with the sensor so that the gain of the amplifier 22 is a simple ratio of two complex admittances. A DC bias circuit 28 provides DC stabilization to the amplifier 22. The amplifier input admittance is the capacitive sensor 2 and the feedback admittance is a reference capacitor 30 resulting in a gain proportional to sensor admittance and inversely proportional to feedback admittance. A digitally synthesized sinusoidal waveform from a first synthesizer 32 is passed through a circuitry gain buffer 34 and input to the virtual ground amplifier via sensor 2. The amplifier output waveform has a sinusoidal element in phase with the input sinusoid and an amplitude directly proportional to the shunt-mode sensor capacitance and another element 90° out of phase with the input sinusoid and an amplitude directly proportional to the dielectric loss of the sensor. This signal is input to a synchronous demodulator 36 such as an analog multiplier whose other input is a second digitally synthesized sinusoid from a synthesizer 38 driven by the same reference oscillator 40 (FIG. 5) which drives the first synthesizer 32 resulting in an unvarying phase relationship between the two. The second frequency synthesizer, under control of a CPU 42 as will be discussed below in conection with FIG. 6, can be in phase or 90° out of phase with the first frequency synthesizer 32 for demodulation of either capacitance or dielectric loss signals, respectively. Using the analog multiplier as a synchronous demodulator results in the desired DC output as well as an unwanted component at twice the input frequency. A low pass filter 44 removes the unwanted component before the signal is passed to an A/D converter 46.

Figure 6:
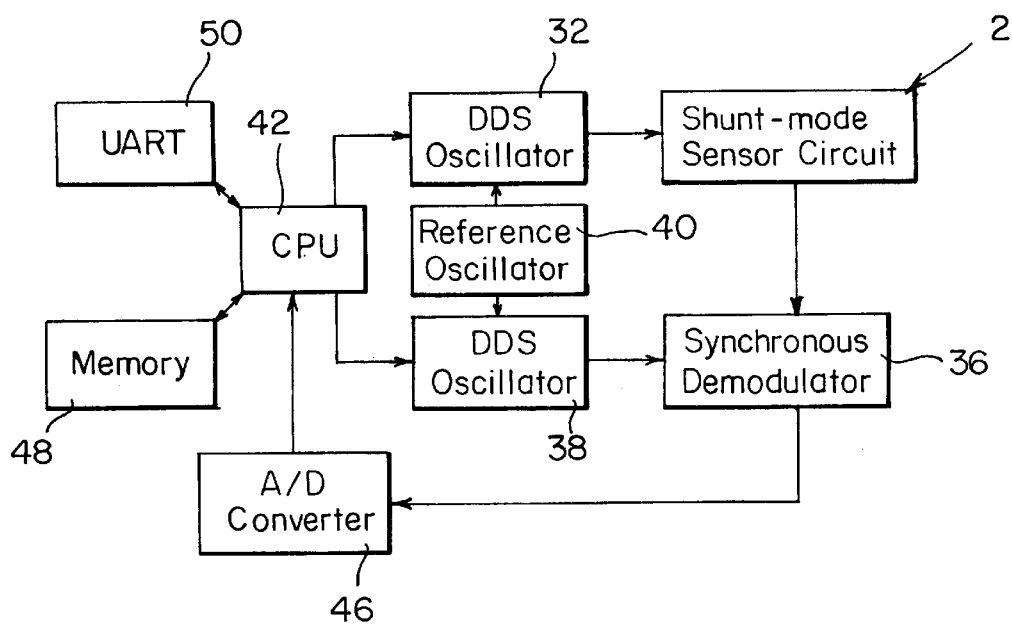
FIG. 6 is a block diagram of a multi-frequency sensor system according to a preferred embodiment of the invention.

Referring now to FIG. 6, the processing of the output signal from the sensor 2 will be described. A CPU 42 is used to set the first and second digital frequency synthesizers 32, 38 shown in FIG. 5 to a first frequency, both synthesizers being in the same phase. The CPU receives the digital signal from the A/D converter 46 corresponding with the change in capacitance of the capacitive sensor at the first frequency resulting from a particulate sample arranged within or passing by the sensor. The CPU compensates the signals for circuit drift and mechanical variations in the sensor configuration and stores the first signal in a memory 48. The CPU then shifts the digital frequency synthesizer 38 connected with the demodulator 36 by 90° and a second measurement from the sensor is made corresponding with the dielectric loss. The second measurement is also compensated for drift and stored in the memory. The process is repeated for different frequencies between 1.0 khz and 10 MHz and at voltages less than 5V RMS resulting in a plurality of signals being stored in the memory.

The digital dielectric property signals obtained by the sensor and stored in the memory can be converted to a serial data stream by the UART device 50 and transmitted by any number of formats. For example, R5-485 protocol may be used in order to network multiple sensors on a single pair of data lines. The transmitted data is processed in the CPU to identify the sample material and its characteristics. Algorithms are used for moisture and density measurements of the sample and for material identification While in accordance with the provisions of the patent statute the preferred forms and embodiments of the invention have been illustrated and described, it will be apparent to those of ordinary skill in the art that various changes and modifications may be made without deviating from the inventive concepts set forth above.

What is claimed is:

1. A method for determining the material properties of a particulate sample, comprising the steps of
    (a) arranging a shunt-mode dielectric capacitance sensor within a quantity of the particulate sample;
    (b) repeatedly applying at least one sinusoidal voltage signal at different frequencies to the sensor to produce changes in the electrical properties of the sensor as a function of the material properties of the sample;
    (c) determining the changes in electrical properties of the sensor;
    (d) correlating said changes in electrical properties, whereby the material properties including moisture content and density of the sample may be determined; and
    (e) identifying the sample in accordance with said determining and correlating steps.

2. Apparatus for determining the material properties of a particulate sample, comprising
    (a) a shunt-mode dielectric capacitance sensor arranged within a quantity of the particulate sample;
    (b) means comprising a digitally synthesized oscillator and an amplifier for repeatedly applying at least one sinusoidal voltage signal at different frequencies to said sensor to produce changes in the electrical properties of said sensor as a function of the material properties of said sample;
    (c) means for determining the changes in electrical properties of said sensor; and
    (d) means for correlating said changes in electrical properties, whereby the material properties including moisture content and density of the sample are determined.

3. Apparatus for determining the material properties of a particulate sample, comprising
    (a) a shunt-mode dielectric capicitance sensor arranged within a quantity of the particulate sample;
    (b) means for repeatedly applying at least one sinusoidal voltage signal at different frequencies to said sensor to produce changes in the electrical properties of said sensor as a function of the material properties of said sample;
    (c) means for determining the changes in electrical properties of said sensor; and
    (d) microcomputer means for correlating said changes in electrical properties, whereby the material properties including moisture content and density of the sample are determined.

4. Apparatus as defined in claim 3, wherein said microcomputer contains partial least squares algorithm for determining moisture content of the sample.

* * * * *